(12) United States Patent
Malyankar et al.

(10) Patent No.: US 7,521,233 B2
(45) Date of Patent: Apr. 21, 2009

(54) METHODS AND DEVICES FOR PROMOTING ENDOTHELIAL MORPHOGENESIS

(75) Inventors: Uriel M. Malyankar, North Branford, CT (US); Marta Scatena, Seattle, WA (US); Cecilia M. Giachelli, Mill Creek, WA (US)

(73) Assignee: Washington, University of, Seattle, WA (US)

( * ) Notice: Subject to any disclaimer, the term of this patent is extended or adjusted under 35 U.S.C. 154(b) by 0 days.

(21) Appl. No.: 11/675,810

(22) Filed: Feb. 16, 2007

(65) Prior Publication Data

US 2007/0154517 A1 Jul. 5, 2007

Related U.S. Application Data

(62) Division of application No. 10/142,658, filed on May 9, 2002, now Pat. No. 7,198,798.

(60) Provisional application No. 60/290,230, filed on May 10, 2001.

(51) Int. Cl.
*C12N 5/00* (2006.01)
*C07K 14/51* (2006.01)

(52) U.S. Cl. .................. 435/325; 530/350; 530/399; 424/422

(58) Field of Classification Search .................. None
See application file for complete search history.

(56) References Cited

U.S. PATENT DOCUMENTS

| 4,976,734 A | 12/1990 | Urry |
| 6,015,938 A | 1/2000 | Boyle |
| 6,503,184 B1 | 1/2003 | Ni |
| 6,790,823 B1 | 9/2004 | Simonet |

FOREIGN PATENT DOCUMENTS

WO 00/54651 A2 9/2000

OTHER PUBLICATIONS

Griffith, L.G., and G. Naughton, "Tissue Engineering-Current Challenges and Expanding Opportunities," Science 295:1009-1014, 2002.
L'Heureux, N., et al., "Tissue Engineering," Science 284:1621-1622, 1999.
Malyankar, U.M., et al., "Osteoprotegerin Is an αvβ3-Induced, NF-κB-Dependent Survival Factor for Endothelial Cells," Journal of Biological Chemistry 275(28):20959-20962, 2000.
"Angiogenesis," On-Line Medical Dictionary, Published at the Department of Medical Oncology, University of Newcastle Upon Tyne, The CancerWEB Project, Nov. 18, 1997, <http://www.cancerweb.ncl.ac.uk/omd/> [retrieved Feb. 20, 2007].
Post, M.J., et al., "Therapeutic Angiogenesis in Cardiology Using Protein Formulations," Cardiovascular Research 49:522-531, 2001.
Schoppet, M., et al., "RANK Ligand and Osteoprotegerin: Paracrine Regulators of Bone Metabolism and Vascular Function," Arteriosclerosis, Thrombosis, and Vascular Biology 22:549-553, 2002.
Yamaguchi, K., et al., "Characterization of Structural Domains of Human Osteoclastogenesis Inhibitory Factor," Journal of Biological Chemistry 273(9):5117-5123, 1998.
Ortenwall, P., et al., "Endothelial Cell Seeding Reduces Thrombogenicity of Dacron Grafts in Humans," Journal of Vascular Surgery 11(3):403-410, Mar. 1990.
Zilla, P., et al., "Endothelial Cell Transplantation," Seminars in Vascular Surgery 12(1):52-63, Mar. 1999.

*Primary Examiner*—Marianne P Allen
*Assistant Examiner*—Regina M DeBerry
(74) *Attorney, Agent, or Firm*—Christensen, O'Connor, Johnson, Kindness PLLC

(57) ABSTRACT

In one aspect the present invention provides methods for promoting endothelial morphogenesis. The methods of this aspect of the invention include the step of providing to one or more endothelial cells an amount of an osteoprotegerin sufficient to promote endothelial morphogenesis. The methods of this aspect of the invention can be practiced in vivo or in vitro. In another aspect, the present invention provides implantable medical devices that each include: (a) a device body; and (b) a layer attached to a surface of the device body, the layer comprising a molecule selected from the group consisting of osteoprotegerin and a nucleic acid molecule encoding osteoprotegerin, wherein the device is adapted to be completely or partially implanted into an animal body. The implanted medical device thus promotes the growth of blood vessels in the surrounding tissue, thereby reducing or preventing the formation of a collagenous capsule around the implanted medical device.

9 Claims, 3 Drawing Sheets

SEQUENCE LISTING

```
<160> NUMBER OF SEQ ID NOS: 2

<210> SEQ ID NO 1
<211> LENGTH: 1200
<212> TYPE: DNA
<213> ORGANISM: Homo Sapiens
<220> FEATURE:
<221> NAME/KEY: CDS
<222> LOCATION: (1)..(1200)

<400> SEQUENCE: 1 aac aag ttg ctg tgc tgc gcg ctc gtg ttt ctg gac atc tcc att aag      48
Asn Lys Leu Leu Cys Cys Ala Leu Val Phe Leu Asp Ile Ser Ile Lys
1               5                   10                  15 tgg acc acc cag gaa acg ttt cct cca aag tac ctt cat tat gac gaa      96
Trp Thr Thr Gln Glu Thr Phe Pro Pro Lys Tyr Leu His Tyr Asp Glu
            20                  25                  30 gaa acc tct cat cag ctg ttg tgt gac aaa tgt cct cct ggt acc tac     144
Glu Thr Ser His Gln Leu Leu Cys Asp Lys Cys Pro Pro Gly Thr Tyr
        35                  40                  45 cta aaa caa cac tgt aca gca aag tgg aag acc gtg tgc gcc cct tgc     192
Leu Lys Gln His Cys Thr Ala Lys Trp Lys Thr Val Cys Ala Pro Cys
    50                  55                  60 cct gac cac tac tac aca gac agc tgg cac acc agt gac gag tgt cta     240
Pro Asp His Tyr Tyr Thr Asp Ser Trp His Thr Ser Asp Glu Cys Leu
65                  70                  75                  80 tac tgc agc ccc gtg tgc aag gag ctg cag tac gtc aag cag gag tgc     288
Tyr Cys Ser Pro Val Cys Lys Glu Leu Gln Tyr Val Lys Gln Glu Cys
                85                  90                  95 aat cgc acc cac aac cgc gtg tgc gaa tgc aag gaa ggg cgc tac ctt     336
Asn Arg Thr His Asn Arg Val Cys Glu Cys Lys Glu Gly Arg Tyr Leu
            100                 105                 110
```

|  |  |  |  |  |  |  |  |  |  |  |  |  |  |  |  |  |
|---|---|---|---|---|---|---|---|---|---|---|---|---|---|---|---|---|
| gag | ata | gag | ttc | tgc | ttg | aaa | cat | agg | agc | tgc | cct | cct | gga | ttt | gga | 384 |
| Glu | Ile | Glu | Phe | Cys | Leu | Lys | His | Arg | Ser | Cys | Pro | Pro | Gly | Phe | Gly |  |
|  |  | 115 |  |  |  | 120 |  |  |  | 125 |  |  |  |  |  |  |
| gtg | gtg | caa | gct | gga | acc | cca | gag | cga | aat | aca | gtt | tgc | aaa | aga | tgt | 432 |
| Val | Val | Gln | Ala | Gly | Thr | Pro | Glu | Arg | Asn | Thr | Val | Cys | Lys | Arg | Cys |  |
| 130 |  |  |  |  | 135 |  |  |  |  | 140 |  |  |  |  |  |  |
| cca | gat | ggg | ttc | ttc | tca | aat | gag | acg | tca | tct | aaa | gca | ccc | tgt | aga | 480 |
| Pro | Asp | Gly | Phe | Phe | Ser | Asn | Glu | Thr | Ser | Ser | Lys | Ala | Pro | Cys | Arg |  |
| 145 |  |  |  | 150 |  |  |  |  | 155 |  |  |  |  |  | 160 |  |
| aaa | cac | aca | aat | tgc | agt | gtc | ttt | ggt | ctc | ctg | cta | act | cag | aaa | gga | 528 |
| Lys | His | Thr | Asn | Cys | Ser | Val | Phe | Gly | Leu | Leu | Leu | Thr | Gln | Lys | Gly |  |
|  |  |  |  | 165 |  |  |  | 170 |  |  |  |  | 175 |  |  |  |
| aat | gca | aca | cac | gac | aac | ata | tgt | tcc | gga | aac | agt | gaa | tca | act | caa | 576 |
| Asn | Ala | Thr | His | Asp | Asn | Ile | Cys | Ser | Gly | Asn | Ser | Glu | Ser | Thr | Gln |  |
|  |  |  | 180 |  |  |  |  | 185 |  |  |  |  | 190 |  |  |  |
| aaa | tgt | gga | ata | gat | gtt | acc | ctg | tgt | gag | gag | gca | ttc | ttc | agg | ttt | 624 |
| Lys | Cys | Gly | Ile | Asp | Val | Thr | Leu | Cys | Glu | Glu | Ala | Phe | Phe | Arg | Phe |  |
|  |  | 195 |  |  |  |  | 200 |  |  |  |  | 205 |  |  |  |  |
| gct | gtt | cct | aca | aag | ttt | acg | cct | aac | tgg | ctt | agt | gtc | ttg | gta | gac | 672 |
| Ala | Val | Pro | Thr | Lys | Phe | Thr | Pro | Asn | Trp | Leu | Ser | Val | Leu | Val | Asp |  |
|  | 210 |  |  |  |  | 215 |  |  |  |  | 220 |  |  |  |  |  |
| aat | ttg | cct | ggc | acc | aaa | gta | aac | gca | gag | agt | gta | gag | agg | ata | aaa | 720 |
| Asn | Leu | Pro | Gly | Thr | Lys | Val | Asn | Ala | Glu | Ser | Val | Glu | Arg | Ile | Lys |  |
| 225 |  |  |  |  | 230 |  |  |  |  | 235 |  |  |  |  | 240 |  |
| cgg | caa | cac | agc | tca | caa | gaa | cag | act | ttc | cag | ctg | ctg | aag | tta | tgg | 768 |
| Arg | Gln | His | Ser | Ser | Gln | Glu | Gln | Thr | Phe | Gln | Leu | Leu | Lys | Leu | Trp |  |
|  |  |  |  | 245 |  |  |  |  | 250 |  |  |  |  | 255 |  |  |
| aaa | cat | caa | aac | aaa | gcc | caa | gat | ata | gtc | aag | aag | atc | atc | caa | gat | 816 |
| Lys | His | Gln | Asn | Lys | Ala | Gln | Asp | Ile | Val | Lys | Lys | Ile | Ile | Gln | Asp |  |
|  |  |  | 260 |  |  |  |  | 265 |  |  |  |  | 270 |  |  |  |
| att | gac | ctc | tgt | gaa | aac | agc | gtg | cag | cgg | cac | att | gga | cat | gct | aac | 864 |
| Ile | Asp | Leu | Cys | Glu | Asn | Ser | Val | Gln | Arg | His | Ile | Gly | His | Ala | Asn |  |
|  |  | 275 |  |  |  |  | 280 |  |  |  |  | 285 |  |  |  |  |
| ctc | acc | ttc | gag | cag | ctt | cgt | agc | ttg | atg | gaa | agc | tta | ccg | gga | aag | 912 |
| Leu | Thr | Phe | Glu | Gln | Leu | Arg | Ser | Leu | Met | Glu | Ser | Leu | Pro | Gly | Lys |  |
|  | 290 |  |  |  |  | 295 |  |  |  |  | 300 |  |  |  |  |  |
| aaa | gtg | gga | gca | gaa | gac | att | gaa | aaa | aca | ata | aag | gca | tgc | aaa | ccc | 960 |
| Lys | Val | Gly | Ala | Glu | Asp | Ile | Glu | Lys | Thr | Ile | Lys | Ala | Cys | Lys | Pro |  |
| 305 |  |  |  |  | 310 |  |  |  |  | 315 |  |  |  |  | 320 |  |
| agt | gac | cag | atc | ctg | aag | ctg | ctc | agt | ttg | tgg | cga | ata | aaa | aat | ggc | 1008 |
| Ser | Asp | Gln | Ile | Leu | Lys | Leu | Leu | Ser | Leu | Trp | Arg | Ile | Lys | Asn | Gly |  |
|  |  |  |  | 325 |  |  |  |  | 330 |  |  |  |  | 335 |  |  |
| gac | caa | gac | acc | ttg | aag | ggc | cta | atg | cac | gca | cta | aag | cac | tca | aag | 1056 |
| Asp | Gln | Asp | Thr | Leu | Lys | Gly | Leu | Met | His | Ala | Leu | Lys | His | Ser | Lys |  |
|  |  |  | 340 |  |  |  |  | 345 |  |  |  |  | 350 |  |  |  |
| acg | tac | cac | ttt | ccc | aaa | act | gtc | act | cag | agt | cta | aag | aag | acc | atc | 1104 |
| Thr | Tyr | His | Phe | Pro | Lys | Thr | Val | Thr | Gln | Ser | Leu | Lys | Lys | Thr | Ile |  |
|  |  | 355 |  |  |  |  | 360 |  |  |  |  | 365 |  |  |  |  |
| agg | ttc | ctt | cac | agc | ttc | aca | atg | tac | aaa | ttg | tat | cag | aag | tta | ttt | 1152 |
| Arg | Phe | Leu | His | Ser | Phe | Thr | Met | Tyr | Lys | Leu | Tyr | Gln | Lys | Leu | Phe |  |
|  | 370 |  |  |  |  | 375 |  |  |  |  | 380 |  |  |  |  |  |
| tta | gaa | atg | ata | ggt | aac | cag | gtc | caa | tca | gta | aaa | ata | agc | tgc | tta | 1200 |
| Leu | Glu | Met | Ile | Gly | Asn | Gln | Val | Gln | Ser | Val | Lys | Ile | Ser | Cys | Leu |  |
| 385 |  |  |  |  | 390 |  |  |  |  | 395 |  |  |  |  | 400 |  |

<210> SEQ ID NO 2
<211> LENGTH: 400
<212> TYPE: PRT
<213> ORGANISM: Homo Sapiens

<400> SEQUENCE: 2

-continued

```
Asn Lys Leu Leu Cys Cys Ala Leu Val Phe Leu Asp Ile Ser Ile Lys
1               5                   10                  15

Trp Thr Thr Gln Glu Thr Phe Pro Pro Lys Tyr Leu His Tyr Asp Glu
            20                  25                  30

Glu Thr Ser His Gln Leu Leu Cys Asp Lys Cys Pro Pro Gly Thr Tyr
            35                  40                  45

Leu Lys Gln His Cys Thr Ala Lys Trp Lys Thr Val Cys Ala Pro Cys
50                  55                  60

Pro Asp His Tyr Tyr Thr Asp Ser Trp His Thr Ser Asp Glu Cys Leu
65                  70                  75                  80

Tyr Cys Ser Pro Val Cys Lys Glu Leu Gln Tyr Val Lys Gln Glu Cys
                85                  90                  95

Asn Arg Thr His Asn Arg Val Cys Glu Cys Lys Glu Gly Arg Tyr Leu
            100                 105                 110

Glu Ile Glu Phe Cys Leu Lys His Arg Ser Cys Pro Pro Gly Phe Gly
            115                 120                 125

Val Val Gln Ala Gly Thr Pro Glu Arg Asn Thr Val Cys Lys Arg Cys
            130                 135                 140

Pro Asp Gly Phe Phe Ser Asn Glu Thr Ser Ser Lys Ala Pro Cys Arg
145                 150                 155                 160

Lys His Thr Asn Cys Ser Val Phe Gly Leu Leu Leu Thr Gln Lys Gly
            165                 170                 175

Asn Ala Thr His Asp Asn Ile Cys Ser Gly Asn Ser Glu Ser Thr Gln
            180                 185                 190

Lys Cys Gly Ile Asp Val Thr Leu Cys Glu Glu Ala Phe Phe Arg Phe
            195                 200                 205

Ala Val Pro Thr Lys Phe Thr Pro Asn Trp Leu Ser Val Leu Val Asp
            210                 215                 220

Asn Leu Pro Gly Thr Lys Val Asn Ala Glu Ser Val Glu Arg Ile Lys
225                 230                 235                 240

Arg Gln His Ser Ser Gln Glu Gln Thr Phe Gln Leu Leu Lys Leu Trp
            245                 250                 255

Lys His Gln Asn Lys Ala Gln Asp Ile Val Lys Lys Ile Ile Gln Asp
            260                 265                 270

Ile Asp Leu Cys Glu Asn Ser Val Gln Arg His Ile Gly His Ala Asn
            275                 280                 285

Leu Thr Phe Glu Gln Leu Arg Ser Leu Met Glu Ser Leu Pro Gly Lys
            290                 295                 300

Lys Val Gly Ala Glu Asp Ile Glu Lys Thr Ile Lys Ala Cys Lys Pro
305                 310                 315                 320

Ser Asp Gln Ile Leu Lys Leu Leu Ser Leu Trp Arg Ile Lys Asn Gly
            325                 330                 335

Asp Gln Asp Thr Leu Lys Gly Leu Met His Ala Leu Lys His Ser Lys
            340                 345                 350

Thr Tyr His Phe Pro Lys Thr Val Thr Gln Ser Leu Lys Lys Thr Ile
            355                 360                 365

Arg Phe Leu His Ser Phe Thr Met Tyr Lys Leu Tyr Gln Lys Leu Phe
            370                 375                 380

Leu Glu Met Ile Gly Asn Gln Val Gln Ser Val Lys Ile Ser Cys Leu
385                 390                 395                 400
```

METHODS AND DEVICES FOR PROMOTING ENDOTHELIAL MORPHOGENESIS

CROSS-REFERENCE TO RELATED APPLICATION

This application is a divisional of application Ser. No. 10/142,658, filed May 9, 2002, which claims the benefit of Application No. 60/290,230, filed on May 10, 2001.

GOVERNMENT RIGHTS

This invention was made with government support under grant number EEC-9529161 awarded by National Science Foundation; and grant number HL18645, awarded by National Institutes of Health. The government has certain rights in the invention.

FIELD OF THE INVENTION

The present invention relates to methods for promoting the growth of blood vessels.

BACKGROUND OF THE INVENTION

The treatment of many diseases requires the growth of new blood vessels either in vivo or in vitro.

For example, during a heart attack the blood supply to a portion of the heart muscle is interrupted and the affected muscle dies or is injured. A goal of medical research is to develop methods to promote the growth of new blood vessels into, and around, the damaged heart tissue to aid its recovery.

Again by way of example, there is a continuing need for methods that promote the formation of blood vessels in vitro. These cultured blood vessels can be used to surgically repair or replace damaged blood vessels in an animal body. For example, cultured blood vessels can be used to repair blood vessel aneurisms.

Again by way of example, the implantation of a medical device into an animal body elicits a wound response. This type of wound response is called the foreign body response and results in the encapsulation of the implant by a poorly-vascularized, collagenous, capsule that can compromise the function of the implant. Formation of the collagenous capsule can be slowed or prevented by promoting the growth of blood vessels in the tissue surrounding the implanted device. There is, therefore, a continuing need for methods that promote the growth of blood vessels into the tissue surrounding implanted medical devices.

Large blood vessels, such as arteries and veins, include an endothelial lining surrounded by other tissue layers, such as a layer of muscle cells that regulate the diameter of the vessel, and thereby regulate blood pressure within the vessel. Some small blood vessels, such as capillaries, are made entirely from endothelial cells. The present invention provides methods for promoting endothelial morphogenesis, which is the formation of an animal anatomical structure from endothelial cells. Thus, the methods of the present invention can be used to promote the formation of new blood vessels, such as capillaries, that are composed entirely of endothelial cells; and also can be used to promote the formation of endothelial portions of blood vessels, such as promoting the formation of an endothelial lining in the lumen of an artificial blood vessel.

The present invention also provides implantable medical devices that promote endothelial morphogenesis, including the formation of new blood vessels, in the living tissue that completely, or partially, surrounds the device after implantation into an animal body. As described more fully herein, the methods and devices of the invention utilize osteoprotegerin protein, or biologically active fragments thereof, to promote endothelial morphogenesis.

SUMMARY OF THE INVENTION

In accordance with the foregoing, in one aspect the present invention provides methods for promoting endothelial morphogenesis. The methods of this aspect of the invention include the step of providing to one or more endothelial cells an amount of an osteoprotegerin sufficient to promote endothelial morphogenesis. In this context, the term "endothelial cells" encompasses endothelial stem cells and differentiated endothelial cells. Examples of endothelial morphogenesis include the formation of capillaries from endothelial cells, and the formation of the endothelial lining of arteries and veins. The methods of this aspect of the invention can be practiced in vivo or in vitro. Exemplary methods for providing osteoprotegerin to one or more endothelial cells include: direct injection of osteoprotegerin into, or close to, a target site within an animal body; secretion of osteoprotegerin from cells adjacent to the target endothelial cells (e.g., by grafting tissue that secretes osteoprotegerin onto, or close to, the target endothelial cells); or by attachment of osteoprotegerin to a surface of a medical device that is implanted at, or close to, the site of the target endothelial cells within an animal body.

As described more fully herein, the methods of the invention are useful in any situation where promotion of endothelial morphogenesis is desired, such as promotion of blood vessel growth in and around damaged heart muscle.

In another aspect, the present invention provides implantable medical devices that each include: (a) a device body; and (b) a layer attached to a surface of the device body, the layer comprising a molecule (typically a multiplicity of molecules) selected from the group consisting of (1) a nucleic acid molecule encoding osteoprotegerin (e.g., the nucleic acid molecule having the sequence set forth in SEQ ID NO: 1), and (2) osteoprotegerin (e.g., the osteoprotegerin having the sequence set forth in SEQ ID NO:2), wherein the device is adapted to be completely or partially implanted into an animal body. The implanted medical device promotes the growth of blood vessels in the surrounding tissue, thereby reducing or preventing the formation of a collagenous capsule around the implanted medical device. As described more fully herein, the implantable medical devices of the invention are useful in any situation where promotion of endothelial morphogenesis is desired, such as promotion of blood vessel growth in tissue surrounding the implanted device, thereby reducing or preventing the foreign body reaction.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

growing into polyvinyl alcohol sponges implanted into mice. The sponges had been soaked in one of the following solutions: a solution of bovine fibroblast growth factor (bFGF); a solution of the Fc portion of human IgG (FC); and a solution of a hybrid protein composed of the Fc portion of human IgG fused to osteoprotegerin (OPG-FC). The control was a sponge soaked in phosphate buffered saline (PBS). This experiment is described in Example 1.

Figure 5:
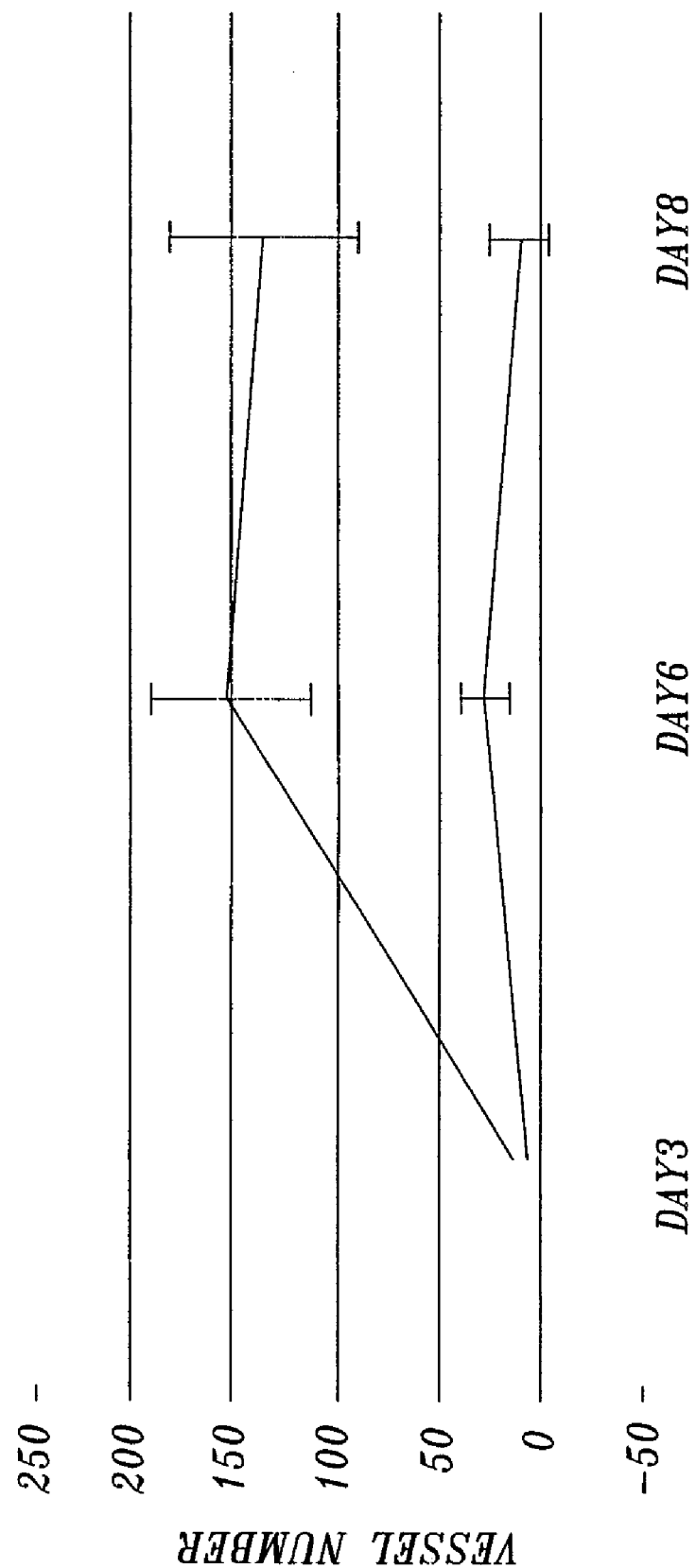

FIG. 5 shows the number of blood vessels growing from excised portions of mouse aortic arch into collagen gel containing osteoprotegerin (OPG), and the number of blood vessels growing from excised portions of mouse aortic arch into control collagen gel that does not contain osteoprotegerin. This experiment is described in Example 2.

DETAILED DESCRIPTION OF THE PREFERRED EMBODIMENT

Unless specifically defined herein, all terms used herein have the same meaning as they would to one skilled in the art of the present invention. Practitioners are particularly directed to Sambrook et al. (1989) *Molecular Cloning: A Laboratory Manual, 2nd ed.*, Cold Spring Harbor Press, Plainsview, N.Y. (1989), for definitions and terms of the art. Unless stated otherwise, all publications and patents that are cited in the present patent application are incorporated herein by reference in their entirety.

As used herein, the term "endothelial morphogenesis" means the formation of an animal anatomical structure (e.g., capillaries and the endothelial lining of the lumen of arteries and veins) from endothelial cells. In this context, the term "endothelial cells" encompasses endothelial stem cells and differentiated endothelial cells.

As used herein, the term "osteoprotegerin", refers to an art-recognized class of proteins (and their functional sequence variants) that are members of the tumor necrosis factor receptor (TNFR) superfamily, and that possess several biological activities in vivo, including blocking bone resorption, promoting bone formation, and promoting endothelial morphogenesis. Osteoprotegerins are reviewed by Schoppet et al., *Arteriosclerosis, Thrombosis, Vascular Biology* 22:549-553 (2002).

As used herein, the term "percent identity" or "percent identical", when used in connection with osteoprotegerin molecules useful in the practice of the present invention, is defined as the percentage of amino acid residues in an osteoprotegerin molecule sequence that are identical with the amino acid sequence of a specified osteoprotegerin molecule (such as the amino acid sequence of SEQ ID NO:2), after aligning the osteoprotegerin sequences to achieve the maximum percent identity. When making the comparison, no gaps are introduced into the osteoprotegerin sequences in order to achieve the best alignment.

Amino acid sequence identity can be determined, for example, in the following manner. The amino acid sequence of an osteoprotegerin molecule (e.g., the amino acid sequence set forth in SEQ ID NO:2) is used to search a protein sequence database, such as the GenBank database (accessible at web site http://www.ncbi.nln.nih.gov/blast/), using the BLASTP program. The program is used in the ungapped mode. Default filtering is used to remove sequence homologies due to regions of low complexity. The default parameters of BLASTP are utilized.

As used herein, the term "implantable medical device" refers to medical devices that are adapted to be implanted into the body of an animal, such as a mammal, including a human, during the normal operation of the device. The devices may be completely or partially implanted into the body of an animal.

In one aspect, the present invention provides methods for promoting endothelial morphogenesis. The methods each include the step of providing to one or more endothelial cells an amount of an osteoprotegerin protein sufficient to promote endothelial morphogenesis. In this context, the term "endothelial cells" encompasses differentiated endothelial cells and endothelial stem cells. The methods of this aspect of the invention can be used in any situation in which promotion of endothelial morphogenesis is desired either in vivo or in vitro. The following are representative examples of useful applications of the methods of this aspect of the invention. The methods of this aspect of the invention can be used to promote formation of blood vessels, such as capillaries, in vivo, such as in and around an area of mammalian heart muscle that has been damaged, such as by reduced blood flow resulting from a heart attack. The methods of this aspect of the invention can be used to promote formation, in vivo, of the endothelial lining of the lumen of veins or arteries; and can be used, in vitro, to promote the formation of an endothelial lining in the lumen of an artificial blood vessel, such as a hollow tube made from a biocompatible material such as Dacron®. In this regard, the following publications disclose methods that can be used to make artificial blood vessels, including artificial blood vessels that include one or more layers of endothelial cells: Griffith, L. G. and Naughton, G., *Science* 295(5557): 1009-1014 (2002); and, L'Heureux, et al., *Science* 284 (5420):1621-1622 (1999). Again by way of example, the methods of this aspect of the invention can be used to promote the formation of blood vessels, such as capillaries, in the tissue surrounding an implanted medical device.

Any osteoprotegerin protein that promotes endothelial morphogenesis is useful in the methods of the present invention. Osteoprotegerin proteins useful in the methods of the present invention include naturally purified osteoprotegerin protein, chemically synthesized osteoprotegerin protein, and osteoprotegerin protein produced by recombinant techniques from a prokaryotic or eukaryotic host, including, for example, bacterial, yeast, insect, mammalian, avian and higher plant cells. Osteoprotegerin fragments that promote endothelial morphogenesis are also useful in the practice of the present invention. For example, osteoprotegerin fragments that include the first four structural domains (located within the first 200 amino acids, counted from the N-terminus, of the complete osteoprotegerin amino acid sequence), as identified by K. Yamaguchi et al., *J. Biol. Chem.* 273(9):5117-5123 (1998), are useful in the practice of the present invention.

Osteoprotegerin, or osteoprotegerin fragments, can be recovered and purified by any useful purification method, including ammonium sulfate or ethanol precipitation, acid extraction, anion or cation exchange chromatography, gel filtration, hydrophobic interaction chromatography, affinity chromatography, hydroxylapatite chromatography, and high performance liquid chromatography. For example, a cDNA molecule encoding an osteoprotegerin can be expressed in microbial cells, such as *E. coli* cells, and purified therefrom. Art-recognized techniques for the purification of proteins and peptides are set forth, for example, in Methods in Enzymology, Vol. 182, Guide to Protein Purification, Murray P. Deutscher, ed (1990).

The cDNA molecule set forth in SEQ ID NO:1 encodes a representative osteoprotegerin (consisting of the amino acid sequence set forth in SEQ ID NO:2) useful in the practice of the invention. Other representative examples of useful osteoprotegerin proteins include osteoprotegerin proteins that are at least 70% identical (such as at least 80% identical, or such as at least 90% identical, or such as at least 95% identical) to the osteoprotegerin protein consisting of the amino acid sequence set forth in SEQ ID NO:2.

In the practice of the invention, osteoprotegerin, or osteoprotegerin fragments, can be provided to endothelial cells in vivo by any useful means, such as by one or more of the following, representative, methods. Osteoprotegerin, or osteoprotegerin fragments, can be introduced into the body by injection at, or close to, the target endothelial cells. Nucleic acid molecules (e.g., cDNA molecules) encoding osteoprotegerin can be delivered into the body of an animal where they are taken up by endothelial cells and expressed therein, or are taken up by cells adjacent to endothelial cells and expressed therein, and the expressed osteoprotegerin secreted so that it stimulates endothelial morphogenesis of the adjacent endothelial cells. The nucleic acid molecules encoding osteoprotegerin can be introduced into the body in the bloodstream, or by injection at, or close to, the target endothelial cells. Genetically engineered cells that secrete osteoprotegerin can be introduced close to the target endothelial cells, for example by grafting genetically engineered tissue that secretes osteoprotegerin close to the target endothelial cells. Osteoprotegerin protein (or osteoprotegerin fragments that retain the ability to promote endothelial morphogenesis) can be introduced to a desired location within an animal body by implanting into the body of an animal a structure comprising osteoprotegerin, or osteoprotegerin peptides retaining the ability to promote endothelial morphogenesis, disposed on a surface of the structure that contacts tissue of the animal body when the structure is implanted therein. Similarly, nucleic acid molecules that encode osteoprotegerin, or osteoprotegerin peptides retaining the ability to promote endothelial morphogenesis, can be non-covalently attached to the surface of an implantable structure which, after implantation into the body, releases the nucleic acid molecules, which are then taken up by adjacent endothelial cells wherein the encoded osteoprotegerin is expressed. For example, representative, art-recognized, methods for introducing osteoprotegerin protein, or osteoprotegerin fragments retaining the ability to promote endothelial morphogenesis, or nucleic acid molecules encoding osteoprotegerin or fragments thereof, into heart tissue are reviewed by M. J. Post et al., *Cardiovascular Research* 49:522-531 (2001).

Osteoprotegerin protein, or osteoprotegerin peptides retaining the ability to promote endothelial morphogenesis, can be delivered into the body of an animal by any suitable means. By way of representative example, osteoprotegerin protein, or fragments thereof, can be introduced into an animal body by application to a bodily membrane capable of absorbing the protein, for example the nasal, gastrointestinal and rectal membranes. The protein is typically applied to the absorptive membrane in conjunction with a permeation enhancer. (See, e.g., V. H. L. Lee, *Crit. Rev. Ther. Drug Carrier Syst.* 5:69 (1988); V. H. L. Lee, *J. Controlled Release* 13:213 (1990); V. H. L. Lee, Ed., *Peptide and Protein Drug Delivery*, Marcel Dekker, New York (1991); A. G. DeBoer et al., *J. Controlled Release* 13:241 (1990)). For example, STDHF is a synthetic derivative of fusidic acid, a steroidal surfactant that is similar in structure to the bile salts, and has been used as a permeation enhancer for nasal delivery. (W. A. Lee, *Biopharm*. Nov./Dec., 22, 1990).

The osteoprotegerin protein, or fragments thereof, may be introduced in association with another molecule, such as a lipid, to protect the protein from enzymatic degradation. For example, the covalent attachment of polymers, especially polyethylene glycol (PEG), has been used to protect certain proteins from enzymatic hydrolysis in the body and thus prolong half-life (F. Fuertges, et al., *J. Controlled Release*, 11:139 (1990)). Many polymer systems have been reported for protein delivery (Y. H. Bae, et al., *J. Controlled Release* 9:271 (1989); R. Hori, et al., *Pharm. Res.* 6:813 (1989); I. Yamakawa, et al., *J. Pharm. Sci.* 79:505 (1990); I. Yoshihiro, et al., *J. Controlled Release* 10:195 (1989); M. Asano, et al., *J. Controlled Release* 9:111 (1989); J. Rosenblatt et al., *J. Controlled Release* 9:195 (1989); K. Makino, *J. Controlled Release* 12:235 (1990); Y. Takakura et al., *J. Pharm. Sci.* 78:117 (1989); Y. Takakura et al., *J. Pharm. Sci.* 78:219 (1989)).

For transdermal applications, the osteoprotegerin protein, or fragments thereof, may be combined with other suitable ingredients, such as carriers and/or adjuvants. There are no limitations on the nature of such other ingredients, except that they must be pharmaceutically acceptable and efficacious for their intended administration, and cannot degrade the activity of the active ingredients of the composition. Examples of suitable vehicles include ointments, creams, gels, or suspensions, with or without purified collagen. The osteoprotegerin protein, or fragments thereof, also may be impregnated into transdermal patches, plasters, and bandages, preferably in liquid or semi-liquid form.

Again by way of example, in the practice of the invention, osteoprotegerin, or osteoprotegerin fragments, can be provided to endothelial cells by delivery of nucleic acid molecules encoding osteoprotegerin, or a biologically active fragment thereof, which are taken up by endothelial cells (or cells adjacent to the target endothelial cells), and expressed therein. If the nucleic acid molecules are taken up and expressed by cells adjacent to the target endothelial cells, then the expressed osteoprotegerin is secreted and interacts with the target endothelial cells to promote endothelial morphogenesis. The nucleic acid molecule can also be introduced into host cells, in vitro, and the modified cells introduced into the body of an animal (e.g., by grafting) wherein they express and secrete osteoprotegerin.

Examples of nucleic acid molecules that encode osteoprotegerin, or fragment thereof, and that are useful in the methods of the invention (and in the devices of the invention) include nucleic acid molecules that encode an osteoprotegerin, or fragment thereof, and that hybridize under conditions of 5×SSC at 60° C. for 30 minutes to the complement of the nucleic acid molecule set forth in SEQ ID NO:1. Some nucleic acid molecules that encode an osteoprotegerin and that are useful in the practice of the present invention hybridize under conditions of 2×SSC at 60° C. for 30 minutes to the complement of the nucleic acid molecule set forth in SEQ ID NO:1. Some nucleic acid molecules that encode an osteoprotegerin and that are useful in the practice of the present invention hybridize under conditions of 1×SSC at 60° C. for 30 minutes to the complement of the nucleic acid molecule set forth in SEQ ID NO:1. Some nucleic acid molecules that encode an osteoprotegerin and that are useful in the practice of the present invention hybridize under conditions of 0.5× SSC at 60° C. for 30 minutes to the complement of the nucleic acid molecule set forth in SEQ ID NO:1.

Hybridization can be conducted, for example, by utilizing the technique of hybridizing radiolabelled nucleic acid probes to nucleic acids immobilized on nitrocellulose filters or nylon membranes as set forth at pages 9.52 to 9.55 of *Molecular Cloning, A Laboratory Manual* (2nd edition), J. Sambrook, E. F. Fritsch and T. Maniatis eds, the cited pages of which are incorporated herein by reference. An exemplary hybridization protocol is set forth in Example 3 herein.

The nucleic acid molecule is typically part of a vector that typically includes all of the necessary elements for expression of the encoded osteoprotegerin, or encoded osteoprotegerin fragment. Any art-recognized nucleic acid delivery method can be used to introduce a vector into one or more cells for expression therein, including: transduction, transfection, transformation, direct injection, electroporation, virus-mediated gene delivery, amino acid-mediated gene delivery, biolistic gene delivery, lipofection and heat shock. See, generally, Sambrook et al, supra. Representative, non-viral, methods of gene delivery into cells are disclosed in Huang, L., Hung, M-C, and Wagner, E., Non-Viral Vectors for Gene Therapy, Academic Press, San Diego, Calif. (1999).

Expression vectors useful for expressing osteoprotegerin protein, or biologically active fragments thereof, include chromosomal, episomal, and virus-derived vectors, e.g., vectors derived from bacterial plasmids, bacteriophages, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids. In certain embodiments in this regard, the vectors provide for specific expression, which may be inducible and/or cell type-specific. Among such expression vectors are those inducible by environmental factors that are easy to manipulate, such as temperature and nutrient additives.

For example, a coding sequence for osteoprotegerin, or a biologically active fragment thereof, can be introduced into cells in situ, or after removal of the cells from the body, by means of viral vectors. For example, retroviruses are RNA viruses that have the ability to insert their genes into host cell chromosomes after infection. Retroviral vectors have been developed that lack the genes encoding viral proteins, but retain the ability to infect cells and insert their genes into the chromosomes of the target cell (see, A. D. Miller, Hum. Gen. Ther. 1:5-14 (1990)). Adenoviral vectors are designed to be administered directly to patients. Unlike retroviral vectors, adenoviral vectors do not integrate into the chromosome of the host cell. Instead, genes introduced into cells using adenoviral vectors are maintained in the nucleus as an extrachromosomal element (episome) that persists for a limited time period. Adenoviral vectors will infect dividing and non-dividing cells in many different tissues in vivo including airway epithelial cells, endothelial cells, hepatocytes and various tumors (B. C. Trapnell, Adv Drug Del Rev. 12:185-199 (1993)).

Another useful viral vector is the herpes simplex virus; a large, double-stranded DNA virus. Recombinant forms of the vaccinia virus can accommodate large inserts and are generated by homologous recombination. To date, this vector has been used to deliver, for example, interleukins (ILs), such as human IL-1β and the costimulatory molecules B7-1 and B7-2 (G. R. Peplinski et al., Ann. Surg. Oncol. 2:151-9 (1995); J. W. Hodge et al., Cancer Res. 54:5552-55 (1994)).

A plasmid vector can be introduced into mammalian cells by any art-recognized means, such as in a precipitate, such as a calcium phosphate precipitate, or in a complex with a charged lipid (e.g., LIPOFECTAMINE™; Life Technologies, Inc.; Rockville, Md.) or in a complex with a virus (such as an adenovirus) or components of a virus (such as viral capsid peptides). If the vector is a virus, it may be packaged in vitro using an appropriate packaging cell line and then transduced into host cells.

For example, a vector may be formulated for delivery either encapsulated in a lipid particle, a liposome, a vesicle, or a gene activated collagen matrix. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers.

Some liposomes have improved serum stability and circulation half-times (see, e.g., U.S. Pat. No. 5,741,516). Furthermore, various methods of liposome and liposome-like preparations as potential drug carriers have been reviewed (see, e.g., U.S. Pat. Nos. 5,567,434; 5,552,157; 5,565,213; 5,738, 868 and 5,795,587).

Additionally, studies have demonstrated that intramuscular injection of plasmid DNA formulated with 5% PVP (50, 000 kDa) increases the level of reporter gene expression in muscle as much as 200-fold over the levels found with injection of DNA in saline alone (R. J. Mumper et al., Pharm. Res. 13:701-709 (1996); R. J. Mumper et al., Proc. Intern. Symp. Cont. Rol. Bioac. Mater. 22:325-326 (1995)). Intramuscular administration of plasmid DNA results in gene expression that lasts for many months (J. A. Wolff et al., Hum. Mol. Genet. 1:363-369 (1992); M. Manthorpe et al., Hum. Gene Ther. 4:419-431 (1993); G. Ascadi et al., New Biol. 3:71-81 (1991), D. Gal et al., Lab. Invest. 68:18-25 (1993)).

Various devices have been developed for providing nucleic acid molecules (e.g., DNA) to a target cell. One approach is to contact the target cell physically with a catheter that directs nucleic acid molecules to the target cell; or to contact the target cell with an implantable material that includes nucleic acid molecules disposed therein or thereon (see, G. D. Chapman et al., Circulation Res. 71:27-33 (1992)). Another exemplary method for providing nucleic acid molecules to a target cell involves using a fibrous collagen implant material that is soaked in a solution of nucleic acid molecules (e.g., DNA) before being placed at the target site.

Another approach is to utilize needle-free, jet injection devices which project a column of liquid directly into the target tissue under high pressure. (P. A. Furth et al., Anal. Biochem. 20:365-368 (1992); H. L. Vahlsing et al., J. Immunol. Meth. 175:11-22 (1994); F. D. Ledley et al., Cell Biochem. 18A:226 (1994)).

Another device for providing nucleic acid molecules to a target cell is the "gene gun", a ballistic device that projects micro-particles coated with nucleic acid molecules directly into the nucleus of cells in vivo. Once within the nucleus, the nucleic acid molecules dissolve from the gold or tungsten microparticle and can be expressed by the target cell. This method has been used effectively to transfer genes directly into the skin, liver and muscle (N. S. Yang et al., Proc. Natl. Acad. Sci. 87:9568-9572 (1990); L. Cheng et al., Proc. Natl. Acad. Sci. USA. 90:4455-4459 (1993); R. S. Williams et al., Proc. Natl. Acad. Sci. 88:2726-2730 (1991)). Thus, for example, a "gene gun" can be used to introduce a vector comprising a nucleic acid molecule encoding an osteoprotegerin into heart muscle tissue in culture, and the treated tissue can be grafted onto, or close to, the damaged portion of an animal heart to promote formation of new blood vessels.

Osteoprotegerin proteins, or fragments thereof, may be immobilized onto (or within) a surface of an implantable medical device. The modified surface will typically be in contact with living tissue after implantation into an animal body. Such implantable medical devices can be made from, for example, nitrocellulose, diazocellulose, glass, polystyrene, polyvinylchloride, polypropylene, polyethylene, dextran, Sepharose, agar, starch, and nylon. Linkage of the protein to a device can be accomplished by any technique that does not destroy the biological activity of the linked protein, for example by attaching one or both ends of the protein (i.e., the N-terminal of the protein, and/or the C-terminal of the protein) to the device. Attachment may also be made at one or more internal sites in the protein. Multiple attachments (both internal and at the ends of the protein) may also be used. A surface of an implantable medical device can be modified to include functional groups (e.g., carboxyl, amide, amino, ether, hydroxyl, cyano, nitrido, sulfanamido, acetylinic, epoxide, silanic, anhydric, succinimic, azido) for protein immobilization thereto. Coupling chemistries include, but are not limited to, the formation of esters, ethers, amides, azido and sulfanamido derivatives, cyanate and other linkages to the functional groups available on osteoprotegerin proteins or fragments. Osteoprotegerin protein, or fragments thereof, can also be attached non-covalently by the addition of an affinity tag sequence to the protein, such as GST (see, Smith, D. B., and Johnson, K. S., Gene 67:31 (1988)), polyhistidines (see, Hochuli, E., et al., J. Chromatog. 411:77 (1987)), or biotin. Such affinity tags may be used for the reversible attachment of the protein to a device. The medical devices of the invention described herein can be used, for example, to deliver osteoprotegerin proteins, or fragments thereof, or nucleic acid molecules encoding osteoprotegerin protein, or fragments thereof, to an animal body.

With respect to the amount of an osteoprotegerin protein (in a solution of osteoprotegerin protein) sufficient to promote endothelial morphogenesis, typically the treatment of a whole animal (e.g., by intravenous injection of an osteoprotegerin protein), or a localized, target population of cells (e.g., by injection of an osteoprotegerin protein at, or close to, a target tissue or organ within an animal body) utilizes an osteoprotegerin solution having an osteoprotegerin concentration in the range of from 0.5 to 5 µg/ml. The dosage regime may be determined empirically without undue experimentation. With respect to the use of an implantable medical device to deliver an effective amount of an osteoprotegerin protein, typically one or more surfaces of the implantable medical device is coated with an osteoprotegerin solution having an osteoprotegerin concentration in the range of from 10 to 100 µg/ml.

In another aspect, the present invention provides implantable medical devices that each include: (a) a device body; and (b) a layer attached to a surface of the device body, the layer including a molecule (typically a multiplicity of molecules) selected from the group consisting of osteoprotegerin and a nucleic acid molecule encoding osteoprotegerin. Osteoprotegerins useful in the methods of the invention (described supra), and nucleic acid molecules encoding osteoprotegerins useful in the methods of the invention (described supra), are also useful in the devices of the invention.

The implantable medical devices of the invention are adapted to be implanted into the body of an animal, such as a mammal, including a human, during the normal operation of the device. The implantable medical devices of the invention may be completely implanted into the body of an animal body (i.e., the entire device is implanted within the body), or the implantable medical devices may be partially implanted into an animal body (i.e., only part of the device is implanted within an animal body, the remainder of the device being located outside of the animal body). Representative examples of completely implantable medical devices include, but are not limited to: cardiovascular devices (such as vascular grafts and stents), artificial blood vessels, artificial bone joints, such as hip joints, and scaffolds that support tissue growth (in such anatomical structures as nerves, pancreas, eye and muscle). Representative examples of partially implantable medical devices include: biosensors (such as those used to monitor the level of drugs within a living body, or the level of blood glucose in a diabetic patient); percutaneous devices (such as catheters) that penetrate the skin and link a living body to a medical device, such as a kidney dialysis machine; and artificial skin that is applied to a damaged area of the skin of an animal body (and thereby penetrates the surface of the body at least by a minimal amount).

Figure 1:
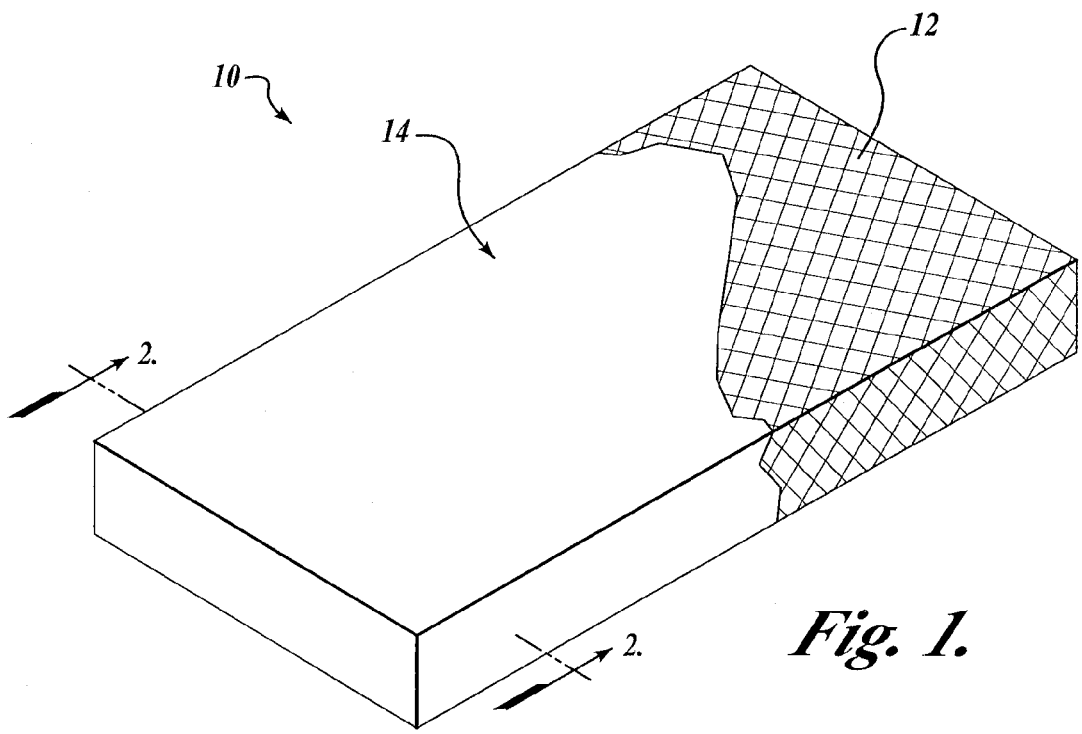
FIG. 1 shows a perspective view of a representative medical device of the invention with a portion of the surface layer removed to expose the underlying device body.

FIG. 1 shows a representative medical device 10 of the present invention, in the form of an implantable drug delivery device, which includes a device body 12 to which is attached a surface layer 14. In the embodiment shown in FIG. 1, surface layer 14 has been partially removed to show device body 12 beneath. Device body 12 is indicated by hatching. As shown in the cross-sectional view of medical device 10 in FIG. 2, surface layer 14 includes a surface layer body 16 that defines an internal surface 18, attached to device body 12, and an external surface 20. Surface layer 14 may completely or partially cover body 12.

Figure 2:
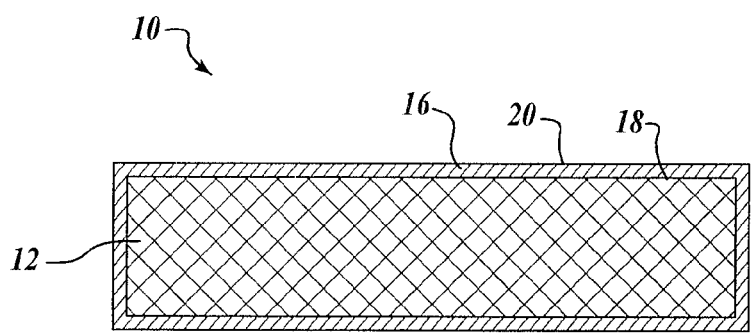
FIG. 2 shows a transverse cross-section of the medical device of FIG. 1.
Figure 3:
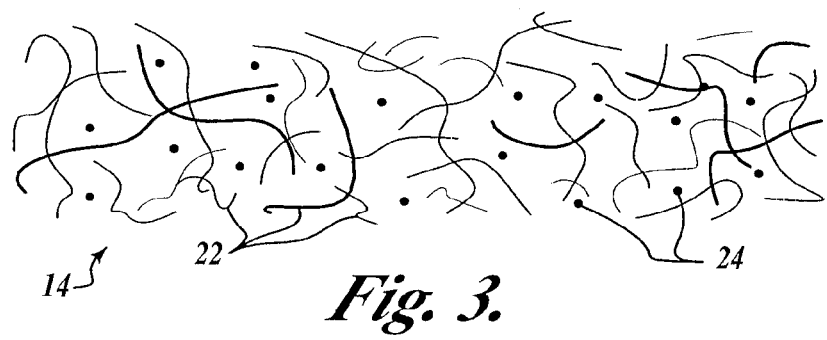
FIG. 3 shows the porous matrix structure of the surface layer of the representative medical device shown in FIG. 1.

In the representative embodiment of device 10 shown in FIGS. 1 and 2, surface layer 14 is made from a porous matrix 22. FIG. 3 shows a representation of porous matrix 22 within which are disposed molecules 24 of osteoprotegerin protein (other molecules, such as drugs, or nucleic acid molecules encoding osteoprotegerin, may also be disposed within porous matrix 22). Thus, in operation, device 10 is implanted into a tissue of an animal body where osteoprotegerin molecules 24 are released over time and promote endothelial morphogenesis.

The following description of the elements of the implantable medical devices of the invention is made with reference to representative device 10 shown in FIGS. 1 and 2, but it will be understood that the following description is applicable to the elements of any implantable medical device of the invention. Device body 12 can be made from any suitable material. Representative examples of synthetic polymers useful for making device body 12 include: (poly)urethane, (poly)carbonate, (poly)ethylene, (poly)propylene, (poly)lactic acid, (poly)galactic acid, (poly)acrylamide, (poly)methyl methacrylate and (poly)styrene. Useful natural polymers include collagen, hyaluronic acid and elastin.

Surface layer 14 can cover the whole of device body 12, or one or more parts of device body 12, such as areas of device body 12 where it is desired to promote endothelial morphogenesis. Surface layer 14 can be made, for example, from any suitable material that: (a) permits deposition therein, or attachment thereto, of osteoprotegerin and/or a nucleic acid molecule that encodes an osteoprotegerin; and (b) can be attached to device body 12 (before or after deposition within, or attachment to, surface layer 14 of osteoprotegerin and/or a nucleic acid molecule that encodes an osteoprotegerin).

Representative examples of materials useful for making surface layer 14 include porous matrices. Representative porous matrices useful for making surface layer 14 include those prepared from tendon or dermal collagen, as may be obtained from a variety of commercial sources, (e.g., Sigma and Collagen Corporation), or collagen matrices prepared as described in U.S. Pat. Nos. 4,394,370 and 4,975,527. One useful collagenous material is termed UltraFiber™, and is obtainable from Norian Corp. (Mountain View, Calif.).

Certain polymeric matrices may also be employed if desired, these include acrylic ester polymers and lactic acid polymers, as disclosed, for example, in U.S. Pat. Nos. 4,526, 909, and 4,563,489. Particular examples of useful polymers are those of orthoesters, anhydrides, propylene-cofumarates, or a polymer of one or more α-hydroxy carboxylic acid monomers, (e.g., α-hydroxy acetic acid (glycolic acid) and/or α-hydroxy propionic acid (lactic acid)).

By way of representative example, osteoprotegerin, and/or fragments thereof that have the ability to promote endothelial morphogenesis, can be covalently attached to surface layer 14 by any of the following pairs of reactive groups (one member of the pair being present on surface layer 14, and the other member of the pair being present on the osteoprotegerin protein(s)): hydroxyl/carboxylic acid to yield an ester linkage; hydroxyl/anhydride to yield an ester linkage; hydroxyl/isocyanate to yield a urethane linkage.

If surface layer 14 does not possess useful reactive groups, then surface layer 14 can be treated, for example, with radiofrequency discharge plasma (RFGD) etching to generate reactive groups in order to allow attachment of osteoprotegerin, or fragments thereof that have the ability to promote endothelial morphogenesis, (e.g., treatment with oxygen plasma to introduce oxygen-containing groups; treatment with propyl amino plasma to introduce amine groups). When an RFGD glow discharge plasma is created using an organic vapor, deposition of a polymeric overlayer occurs on the exposed surface. RFGD plasma deposited films offer several advantages: they are smooth, conformal, and uniform; film thickness is easily controlled and ultrathin films (10-1000 Angstroms) are readily achieved, allowing for surface modification of a material without alteration to its bulk properties. Moreover, plasma films are highly-crosslinked and pin-hole free, and therefore chemically stable and mechanically durable. RFGD plasma deposition of organic thin films has been used in microelectronic fabrication, adhesion promotion, corrosion protection, permeation control, as well as biomaterials. (see, e.g., Ratner, U.S. Pat. No. 6,131,580).

Typically, nucleic acid molecules that encode osteoprotegerin, or encode an osteoprotegerin fragment that has the ability to promote endothelial morphogenesis, are non-covalently attached to surface layer 14, e.g., nucleic acid molecules can be disposed within the pores of a porous material that is used to form surface layer 14. The nucleic acid molecules diffuse out of porous surface layer 14, when device 10 is implanted into an animal body, and are taken up by adjacent cells wherein the osteoprotegerin encoded by the nucleic acid molecules is expressed.

The following examples merely illustrate the best mode now contemplated for practicing the invention, but should not be construed to limit the invention.

EXAMPLE 1

This Example shows that an osteoprotegerin-IgGFc protein fusion is as effective as fibroblast growth factor at inducing the formation of blood vessels in an in vivo impregnated sponge assay.

C57BL6 mice were implanted with polyvinyl alcohol sponges presoaked in one of the following solutions which each had a concentration of 100 ng/ml: a solution of bovine fibroblast growth factor (bFGF); a solution of the Fc portion of human IgG (FC); and a solution of a hybrid protein composed of the Fc portion of human IgG fused to osteoprotegerin (OPG-FC). The control was phosphate buffered saline (PBS).

Figure 4:
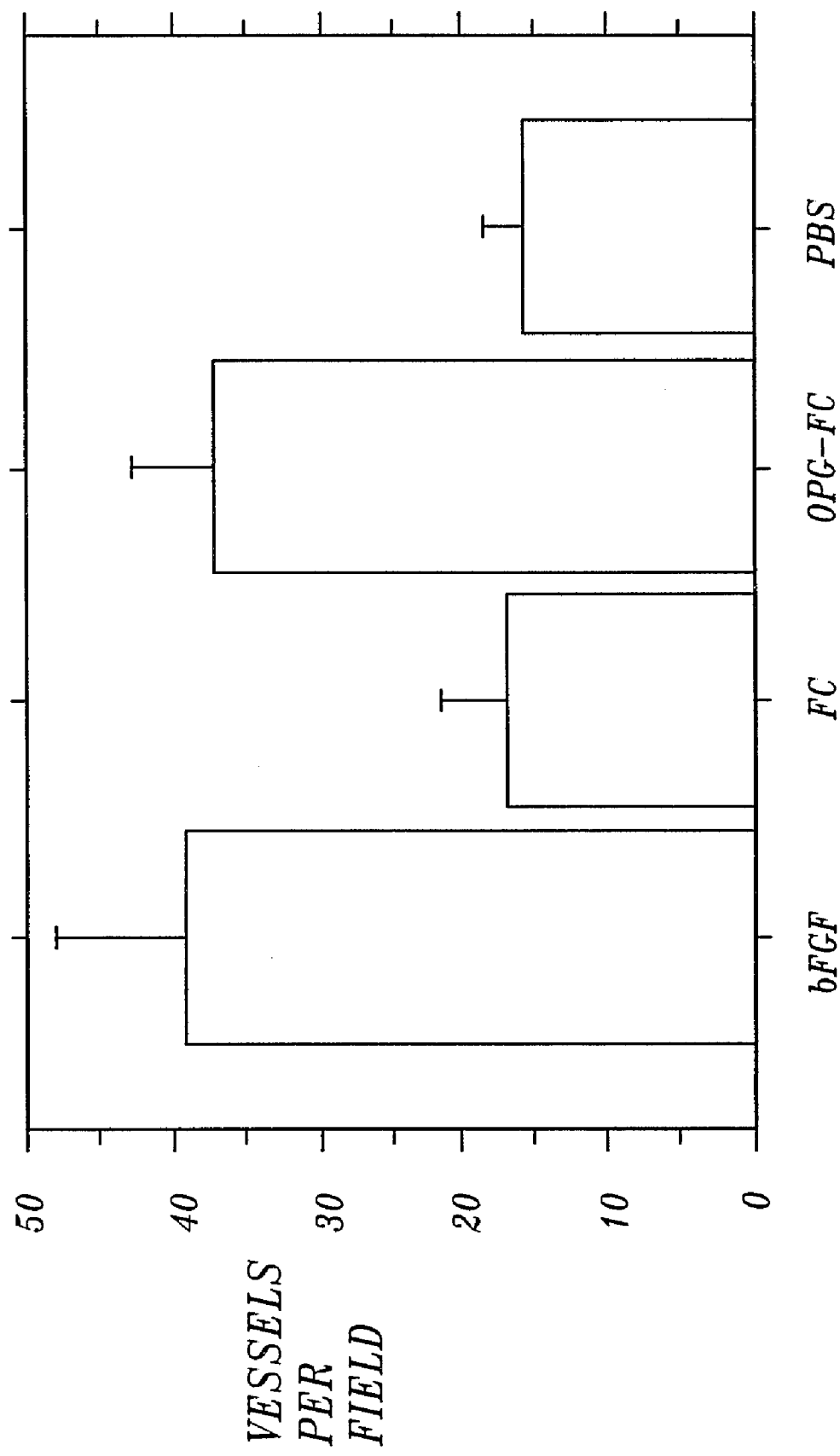
FIG. 4 shows the number of blood vessels (per visual field when viewed under a microscope at 400× magnification)

After the sponges had been implanted subcutaneously in the backs of the mice for a period of fourteen days, the sponges were removed and the number of blood vessels growing into the sponges were counted under a microscope. The results are shown in FIG. 4, and show that osteoprotegerin-IgGFc protein fusion was as effective as fibroblast growth factor at inducing the formation of blood vessels.

EXAMPLE 2

This Example shows that osteoprotegerin protein induces the formation of blood vessels in an in vitro rat aortic ring assay.

Thoracic aorta was excised from five to ten week old Fischer 344 male rats. The periaortic fibroadipose tissue was dissected and the cleaned aorta was cross-sectioned to yield rings of 1-2 mm in length. The rings were embedded in collagen gels. The collagen gels were prepared by mixing eight volumes of 1 mg/ml collagen with one volume of 10× Minimal Essential Medium (MEM, Invitrogen), pH 4.0, and one volume of 23.4 mg/ml $NaHCO_3$. The embedded aortic rings were transferred to 16 mm wells that each contained 0.5 ml of serum-free endothelial basal medium (sold by Invitrogen as MCDB 131). The medium was changed three times per week starting at day three. The cultures were treated with a 140 nM solution of human recombinant osteoprotegerin. The control was aortic sections treated with Phosphate Buffered Saline only. The number of blood vessels growing from the aortic rings into the collagen gel were counted on days 3, 6 and 8 after embedding into the collagen gel.

As shown in FIG. 5, the number of blood vessels growing into the collagen gel was significantly greater in the presence of osteoprotegerin compared to the control culture lacking osteoprotegerin in the gel.

EXAMPLE 3

This example describes a representative hybridization protocol that can be used to identify nucleic acid molecules that encode an osteoprotegerin, or a portion of an osteoprotegerin that has the ability to promote endothelial morphogenesis, and that hybridize to the complement of the nucleic acid molecule consisting of the nucleic acid sequence set forth in SEQ ID NO:1, under defined hybridization conditions. In this Example, the complement of the nucleic acid molecule consisting of the nucleic acid sequence set forth in SEQ ID NO:1 is used as probe.

Hybridization solution should preferably be prepared and filtered through a 0.45-micron disposable cellulose acetate filter. The composition of the hybridization solution is 6×SSC, 5× Denhardt's reagent, 0.5% sodium dodecyl sulfate (SDS), 100 μg/ml denatured, fragmented salmon sperm DNA. The abbreviation "SSC" refers to a buffer used in nucleic acid hybridization solutions. One liter of the 20× (twenty times concentrate) stock SSC buffer solution (pH 7.0) contains 175.3 g sodium chloride and 88.2 g sodium citrate. When $^{32}P$-labeled cDNA or RNA is used as a probe, poly(A)$^+$ RNA at a concentration of 1 μg/ml may be included in the hybridization solution to prevent the probe from binding to T-rich sequences that are found fairly commonly in eukaryotic DNA.

The nitrocellulose filter or nylon membrane containing the target DNA is floated on the surface of a tray of 6×SSC until it becomes thoroughly wetted from beneath. The filter is submerged for about 2 minutes. The wet filter is placed into a heat-sealable bag, and 0.2 ml of hybridization solution is added for each square centimeter of nitrocellulose filter or nylon membrane.

As much air as possible is squeezed from the bag, and the open end of the bag is sealed with a heat sealer. The bag is incubated for 1-2 hours submerged at the desired temperature (typically no higher than the hybridization temperature). It is desirable to agitate the bag.

If the radiolabeled probe is double-stranded, then it should preferably be denatured by heating for 5 minutes at 100° C.

Single-stranded probe need not be denatured. The denatured probe is chilled rapidly in ice water. Ideally, probe having a specific activity of $10^9$ cpm/μg, or greater, is used. Hybridization is carried out for the desired time period (e.g., for a period of from 12 hours to 24 hours) at 50° C., typically using 1-2 μg/ml radiolabeled probe.

The bag containing the filter is removed from the water bath, and the bag is opened by cutting off one corner with scissors. The denatured probe is added to the hybridization solution, and then as much air as possible is squeezed from the bag. The bag is resealed with the heat sealer so that as few bubbles as possible are trapped in the bag. To avoid radioactive contamination of the water bath, the resealed bag should be sealed inside a second, noncontaminated bag.

The bag is submerged in a water bath and incubated for the required period of hybridization. The bag is removed from the water bath and one corner is cut off. The hybridization solution is poured into a container suitable for disposal, and then the bag is cut along the length of three sides. The filter is removed and immediately submerged in a tray containing several hundred milliliters of 2×SSC and 0.5% SDS at room temperature (no higher than 25° C.). The filter should not be allowed to dry out at any stage during the washing procedure.

After 5 minutes, the filter is transferred to a fresh tray containing several hundred milliliters of 2×SSC and 0.1% SDS and incubated for 15 minutes at room temperature (no higher than 25° C.) with occasional gentle agitation. The filter is then washed at the desired stringency, i.e., in the desired concentration of SSC and at the desired temperature for the desired period of time. If, for example, nucleic acid molecules that hybridize to the probe at a temperature of 60° C. in 5×SSC for 30 minutes are sought, then the filter is washed in 5×SSC at 60° C. for 30 minutes, i.e., the radiolabelled probe is washed off nucleic acid molecules (immobilized on the filter) that do not hybridize to the probe under conditions of 5×SSC at 60° C. for 30 minutes. It is understood that the stringency of the hybridization step is not higher than the stringency of the wash step.

After washing, most of the liquid is removed from the filter by placing it on a pad of paper towels. The damp filter is placed on a sheet of Saran Wrap, and adhesive dot labels marked with radioactive ink are applied at several asymmetric locations on the Saran Wrap. These markers serve to align the autoradiograph with the filter. The labels should be covered with Scotch Tape which prevents contamination of the film holder or intensifying screen with the radioactive ink. Radioactive ink is made by mixing a small amount of $^{32}P$ with waterproof black drawing ink.

The filter is covered with a second sheet of Saran Wrap, and the filter is exposed to X-ray film (Kodak XAR-2 or equivalent) to obtain an autoradiographic image. The exposure time should be determined empirically.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for promoting endothelial morphogenesis in vitro, said method comprising the step of providing to endothelial cells cultured on a porous matrix or scaffold that supports tissue growth in vitro an amount of an osteoprotegerin sufficient to promote endothelial morphogenesis.

2. The method of claim 1, wherein the osteoprotegerin is at least 70% identical to the osteoprotegerin consisting of the amino acid sequence set forth in SEQ ID NO: 2.

3. The method of claim 1, wherein the osteoprotegerin is at least 80% identical to the osteoprotegerin consisting of the amino acid sequence set forth in SEQ ID NO: 2.

4. The method of claim 1, wherein the osteoprotegerin is at least 90% identical to the osteoprotegerin consisting of the amino acid sequence set forth in SEQ ID NO: 2.

5. The method of claim 1, wherein the endothelial cells are cultured in a liquid medium that comprises the osteoprotegerin.

6. The method of claim 1, wherein the endothelial morphogenesis is formation of capillaries.

7. The method of claim 1, wherein the endothelial morphogenesis is formation of an endothelial lining in a blood vessel.

8. The method of claim 7, wherein the endothelial lining is formed in an artificial blood vessel.

9. The method of claim 7, wherein the endothelial lining is formed in a natural blood vessel.

* * * * *